(12) United States Patent
Tsukada et al.

(10) Patent No.: US 7,537,589 B2
(45) Date of Patent: May 26, 2009

(54) INTERMITTENT URETHRA SELF-RETAINING CATHETER SET

(75) Inventors: Osamu Tsukada, Ueda (JP); Yasuhiko Nakajima, Hiratsuka (JP)

(73) Assignee: Tsukada Medical Research Co., Ltd., Tokyo (JP)

( * ) Notice: Subject to any disclaimer, the term of this patent is extended or adjusted under 35 U.S.C. 154(b) by 40 days.

(21) Appl. No.: 10/568,434

(22) PCT Filed: Aug. 21, 2003

(86) PCT No.: PCT/JP03/10563
§ 371 (c)(1),
(2), (4) Date: Oct. 3, 2006

(87) PCT Pub. No.: WO2005/018714
PCT Pub. Date: Mar. 3, 2005

(65) Prior Publication Data
US 2008/0051762 A1 Feb. 28, 2008

(51) Int. Cl.
*A61M 27/00* (2006.01)
(52) U.S. Cl. .................. 604/544; 604/347; 604/349
(58) Field of Classification Search .................. 604/544, 604/347, 349
See application file for complete search history.

(56) References Cited

U.S. PATENT DOCUMENTS

| 1,486,957 A | * | 3/1924 | England | 206/209.1 |
| 2,088,678 A | * | 8/1937 | Wylie | 215/231 |
| 5,188,593 A | * | 2/1993 | Martin | 604/43 |

(Continued)

FOREIGN PATENT DOCUMENTS

EP 0371497 A1 6/1990

(Continued)

*Primary Examiner*—Michele Kidwell
*Assistant Examiner*—Ilya Y Treyger
(74) *Attorney, Agent, or Firm*—Sughrue Mion, PLLC (57) ABSTRACT

An intermittent urethra self-retaining catheter set 10 comprises a catheter unit 1, a disinfectant casing 2, and a cap 3. The catheter unit 1 includes a catheter body 11 having an urine-guiding passage 111 and a water-guiding passage 112 that extend along a longitudinal direction and are separated from each other, a balloon 12 attached to a distal end of the catheter body 11 in an inflatable manner and communicated to the water-guiding passage 112, an elastic plug 13 attached to an intermediate portion of the catheter body 11, a branched tube 14 branched from the catheter body 11 above the elastic plug 13 and communicated to the water-guiding passage 112, a reservoir 16 attached to a free end of the branched tube 14 in a collapsible manner for storing a sterilized water 15, an on-off valve 17 attached to an intermediate portion of the branched tube 14, and a reinforcement tube 18 inserted into an upper interior of the urine-guiding passage 111 in the catheter body 11. The disinfectant casing 2 is detachably fitted on the elastic plug in a sealing manner for containing a lower part of the catheter body 11 below the elastic plug 13 and for storing a disinfectant liquid 21. The cap 3 is detachably fitted on a top portion of the catheter body 11 for opening and closing an outlet port 311. The on-off valve 17 is adapted to open and close a passage in which the sterilized water 15 flows between the reservoir 16 and the balloon 12.

7 Claims, 7 Drawing Sheets

U.S. PATENT DOCUMENTS

| | | | | |
|---|---|---|---|---|
| 5,569,184 A | * | 10/1996 | Crocker et al. | 604/509 |
| 5,624,410 A | * | 4/1997 | Tsukada et al. | 604/256 |
| 5,817,067 A | * | 10/1998 | Tsukada | 604/256 |
| 5,916,195 A | | 6/1999 | Eshel et al. | |
| 6,162,201 A | * | 12/2000 | Cohen et al. | 604/250 |
| 6,695,831 B1 | * | 2/2004 | Tsukada et al. | 604/544 |
| 2003/0153899 A1 | | 8/2003 | Eshel et al. | |

FOREIGN PATENT DOCUMENTS

| | | |
|---|---|---|
| EP | 1090656 A1 | 11/2001 |
| JP | 1-35234 B | 7/1989 |
| JP | 9-206370 A | 8/1997 |
| JP | 2587642 Y2 | 12/1998 |
| JP | 2001-500023 A | 1/2001 |
| JP | 2001-104472 A | 4/2001 |
| JP | 2001-309973 A | 11/2001 |

* cited by examiner

INTERMITTENT URETHRA SELF-RETAINING CATHETER SET

FIELD OF THE INVENTION

This invention relates to an intermittent urethra self-retaining catheter set in which a catheter is retained in a urethra intermittently to carry out drainage and more particularly relates to an intermittent urethra self-retaining catheter set suitable for a physical exhaustion user or a hyposthenia user to use by oneself.

BACKGROUND OF THE INVENTION

There is a conventional catheter for purpose of urination to an end of which a balloon is attached. The balloon closely contacts with a catheter body during insertion into a urethra. In order to retain the catheter body in a bladder, sterilized water is injected through a proximal end of the catheter body into the balloon to inflate the balloon, thereby preventing a distal end of the catheter from coming out of the bladder. In the case where such catheter is used for a long period of time, a urinary infectious disease will occur and restrict behavior of a user.

In order to prevent the urinary infection disease and ensure freedom of behavior for a user in a certain extent, a Nelaton's catheter to be used in a self-drainage method has been developed. Since this Nelaton's catheter is not provided on a distal end with a balloon, it is impossible to retain the catheter in a urethra for a long period of time. A user must always carry the Nelaton's catheter in a casing filled with disinfectant liquid. If desired, the user removes the Nelaton's catheter from the casing and inserts the catheter through the urethra into the bladder to drain urine by oneself.

This Nelaton's catheter is inconvenient for a user, because the user must always carry it. It will be unnecessary for a patient suffered with a damaged spinal cord, a patient suffered with a cerebrovascular disease, or a patient suffered with a urination disease due to congenital urethra deformity to retain the catheter in the bladder, if the patient is awake, or if an attendant presents near the patient. On the other hand, if the attendant does not present near the patient, it will be necessary to retain the catheter in the patient's bladder.

In order to obtain an intermittent urethra self-retaining catheter set that has a self-retaining function in a conventional catheter with a balloon and a self-drainage function in a conventional catheter with no balloon (Nelaton's catheter), the present applicant has proposed previously "INTERMITTENT URETHRA SELF-RETAINING CATHETER SET" (Japanese Utility Model Registered Publication No. 2587642). This intermittent urethra self-retaining catheter set comprises a catheter unit, a disinfectant casing, and a cap. The catheter unit includes a catheter body having an urine-guiding passage and a water-guiding passage that extend along a longitudinal direction and are separated from each other, a balloon attached to a distal end of the catheter body in an inflatable manner and communicated to the water-guiding passage, an elastic plug attached to an intermediate portion of the catheter body, a branched tube bifurcated from the catheter body above the elastic plug and communicated to the water-guiding passage, a reservoir attached to a free end of the branched tube in a collapsible manner for storing a sterilized water, and an on-off valve attached to an intermediate portion of the branched tube. The disinfectant casing is detachably fitted on the elastic plug in a sealing manner for containing a lower part of the catheter body below the elastic plug and for storing a disinfectant liquid. The cap is detachably fitted on a top portion of the elastic plug to cover a top of the catheter body above the elastic plug, the branched tube, the on-off valve, and the reservoir.

Although this intermittent urethra self-retaining catheter set has achieved the initial object, it has not been still sufficient for, in particular, a physical exhaustion user or a hyposthenia user to use the catheter set by oneself. Since the catheter body is rich in flexibility, it is difficult for the user to insert the catheter body into the urethra. Furthermore, a user is required for a delicate technique and a slight force in patient's fingers in order to attach and detach the cap to and from the elastic plug and to open and close the on-off valve.

On the other hand, the present applicant has proposed previously "CAP FOR MEDICAL APPLIANCE TO BE RETAINED IN HUMAN BODY" (Japanese Patent Public Publication No. HEI 9-206370 (1997)). The cap for a medical appliance to be retained in a human body is constructed to achieve an object in which the cap can be readily handled for charging and discharging urine even by, for example, a woman who retains urine in her bladder, a person who finds it difficult to discharge urine, or a person who uses urinary bladder bags or napkins due to incompleteness of urine, and which does not cause leakage of urine even if the contact surfaces become rough on account of urine crystals.

The cap for a medical appliance to be retained in a human body includes a lid body, a connection plug body, and a hinge. The lid body is coupled to the connecting plug body through the hinge. The connection plug body, hinge, and lid body are integrally formed of the same synthetic resin material. The lid body is provided on a central area of an inner surface thereof with an engaging member made of a resilient material. The lid body is provided on an end thereof with a pull string.

There will be a possibility of applying the cap for a medical appliance to be retained in a human body to the intermittent urethra self-retaining catheter set mentioned above.

SUMMARY OF THE INVENTION

Accordingly, an object of the present invention is to provide an intermittent urethra self-retaining catheter set that has a self-retaining function in a conventional catheter with a balloon and a self-drainage function in a conventional catheter with no balloon (Nelaton's catheter) and that is suitable for a user in physical exhaustion or a user in hyposthenia to use by oneself.

In order to achieve the above object, an intermittent urethra self-retaining catheter set in accordance with the present invention comprises a catheter unit, a disinfectant casing, and a cap. The catheter unit includes a catheter body having an urine-guiding passage and a water-guiding passage that extend along a longitudinal direction and are separated from each other, a balloon attached to a distal end of the catheter body in an inflatable manner and communicated to the water-guiding passage, an elastic plug attached to an intermediate portion of the catheter body, a branched tube bifurcated from the catheter body above the elastic plug and communicated to the water-guiding passage, a reservoir attached to a free end of the branched tube in a collapsible manner for storing a sterilized water, an on-off valve attached to an intermediate portion of the branched tube, and a reinforcement tube inserted into an upper interior of the urine-guiding passage in the catheter body. The disinfectant casing is detachably fitted on the elastic plug in a sealing manner for containing a lower part of the catheter body below the elastic plug and for storing a disinfectant liquid. The cap is detachably fitted on a top portion of the catheter body for opening and closing an outlet port. The on-off valve is adapted to open and close a passage in which the sterilized water flows between the reservoir and the balloon. The branched tube may be detachably connected to the catheter body.

The cap includes a connection plug body, a hinge section, and a lid that are made of a synthetic resin material integrally together with one another. An engaging member made of a flexible material is mounted on a central portion of an inner surface of the lid. A pull string is attached to an end of the lid. A first annular magnet may be secured to a top surface of the connection plug body and a second annular magnet may be secured to an inner surface of the lid to surround the engaging member.

The on-off valve includes a valve body, a plunger, and a pull string. The valve body includes a recess that supports the plunger to permit the plunger to reciprocate in the recess with a frictional resistance, a first tube communicated to the reservoir, and a second tube communicated to the branched tube. The plunger includes a plunger body that can reciprocate in the recess with a frictional resistance, a flange, and a communication hole. The pull string is bound on the flange of the plunger to form a hoop.

An absorbing material may be mounted on an inner peripheral surface around an upper outlet of the disinfectant casing. A distal end of the catheter body may be formed into a curved configuration.

PREFERRED EMBODIMENTS OF THE INVENTION

Figure 1:
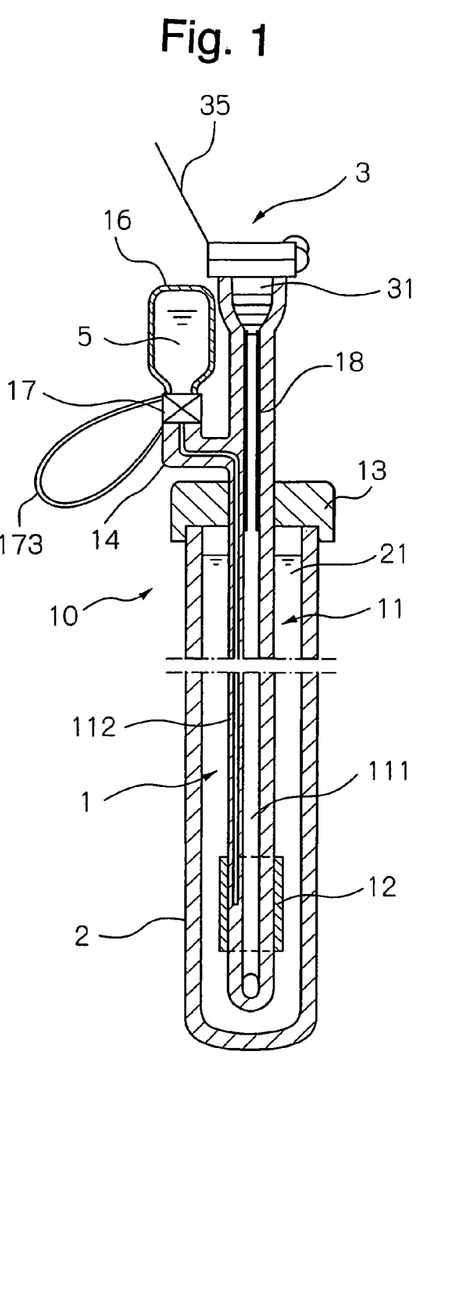
FIG. 1 is a longitudinal section view of an intermittent urethra self-retaining catheter set in accordance with the present invention.
Figure 2:
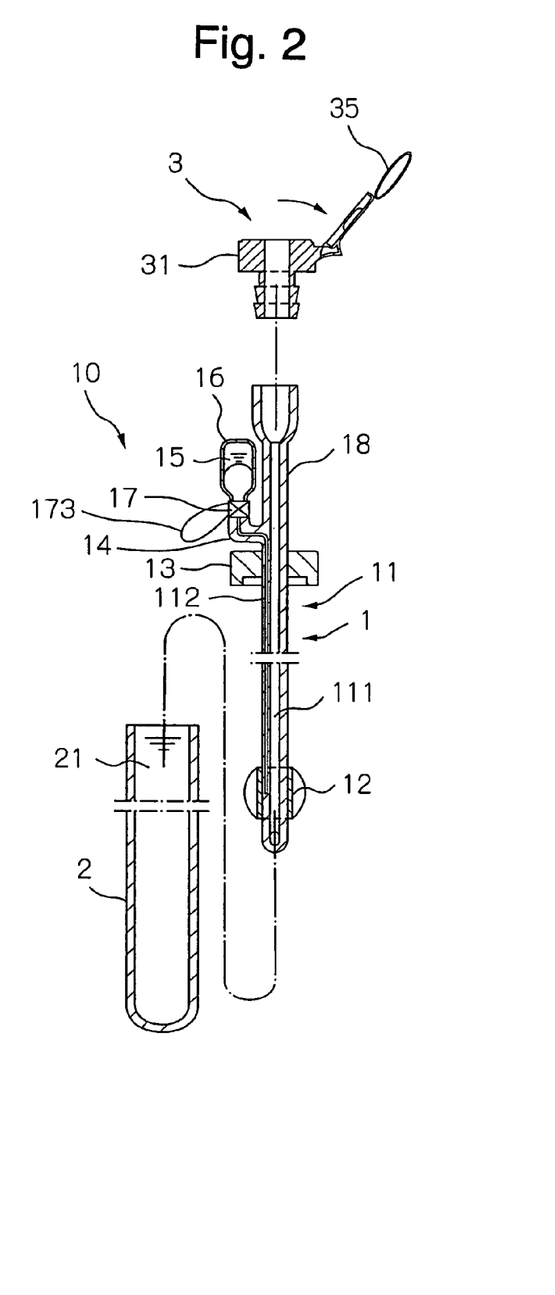
FIG. 2 is an exploded longitudinal section view of the catheter set shown in FIG. 1.

Referring now to the drawings, a preferred embodiment of an intermittent urethra self-retaining catheter set in accordance with the present invention will be described below. As shown in FIGS. 1 and 2, an intermittent urethra self-retaining catheter set 10 of the present invention comprises a catheter unit 1, a disinfectant casing 2, and a cap 3.

The catheter unit 1 includes a catheter body 11 having an urine-guiding passage 111 and a water-guiding passage 112 that extend along a longitudinal direction and are separated from each other, a balloon 12 attached to a distal end of the catheter body 11 in an inflatable manner and communicated to the water-guiding passage 112, an elastic plug 13 attached to an intermediate portion of the catheter body 11, a branched tube 14 bifurcated from the catheter body 11 above the elastic plug 13 and communicated to the water-guiding passage 112, a reservoir 16 attached to a free end of the branched tube 14 in a collapsible manner for storing a sterilized water, an on-off valve 17 attached to an intermediate portion of the branched tube 14, and a reinforcement tube 18 inserted into an upper interior of the urine-guiding passage 111 in the catheter body 11.

The disinfectant casing 2 is detachably fitted on the elastic plug 13 in a sealing manner for containing a lower part of the catheter body 11 below the elastic plug 13 and for storing a disinfectant liquid 21.

The cap 3 is detachably fitted on a top portion of the catheter body 11 for opening and closing the urine-guiding passage 111. The cap 3 can utilize the "CAP FOR MEDICAL APPLIANCE TO BE RETAINED IN HUMAN BODY" (Japanese Patent Public Disclosure No. HEI 9-206370 (1997)) mentioned above. A detailed structure of the cap 3 will be described after by referring to FIGS. 7A, 7B, and 8.

The elastic plug 13 is made of a flexible resin material or the like. The reservoir 16 is made of a flexible resin material such as PVC, polyurethane, or the like. The catheter body 11 and balloon 12 are made of conventional materials. The reinforcement tube 18 is made of a material harder than that of the catheter body 11 (for example, polytetrafluoroetylene, or the like).

The sterilized water 15 may be conventional saline or the like. The disinfectant liquid 21 is preferably benzethonium chloride, for example, a mixture of Hyamine (trade name) sold by SANKYO CO., LTD. and sterilized glycerol liquid; benzallonium chloride, for example, Osvan (trade name) sold by NIHON PHARMACEUTICAL CO., LTD. and TAKEDA CHEMICAL INDUSTRIES, LTD.; or Povidone iodine, for example, Isodine (trade name) sold by MEIJI SEIKA KAISYA, LTD.

Figure 3A:
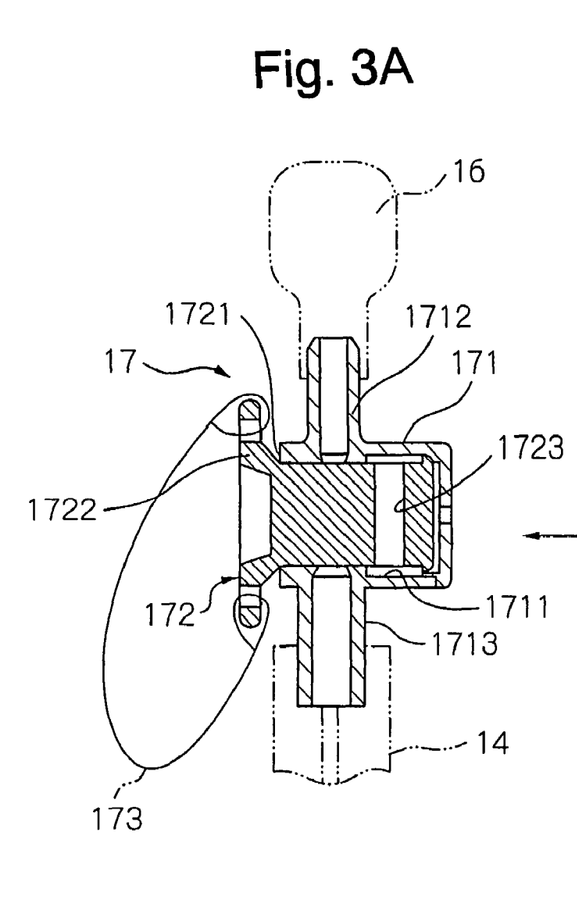
FIG. 3A is a longitudinal section view of an on-off valve to be used in the catheter set of the present invention, illustrating the on-off valve in a closed position.
Figure 3B:
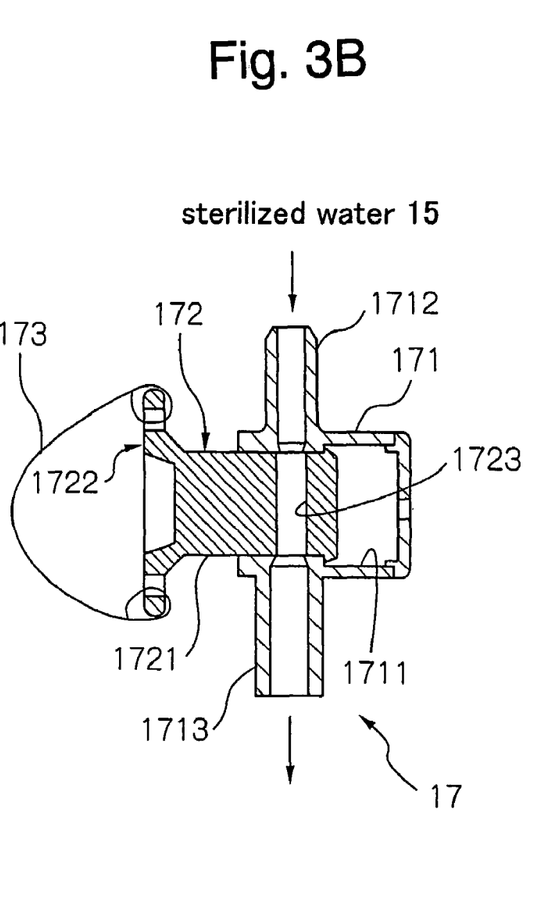
FIG. 3B is a view similar to FIG. 3A, illustrating the on-off valve in an opened position.

FIGS. 3A and 3B show an example of the on-off valve 17. The on-off valve 17 includes a valve body 171, a plunger 172, and a pull string 173. The valve body 171 includes a recess 1711 that supports the plunger 172 to permit the plunger 172 to reciprocate in the recess 1711 with a frictional resistance, a first tube 1712 communicated to the reservoir 16, and a second tube 1713 communicated to the branched tube 14. The plunger 172 includes a plunger body 1721 that can reciprocate in the recess 1711 with a frictional resistance, a flange 1722, and a communication hole 1723. The pull string 173 is bound on the flange 1722 of the plunger 172 to form a hoop.

The on-off valve 17 is set to be in a position shown in FIG. 3A under a normal condition. That is, the plunger body 1721 is inserted into a most inner part of the recess 1711 so that the plunger body 1721 shuts off a communication between the first and second tubes 1712 and 1713. When the pull string 173 is pulled, as shown in FIG. 3B, the plunger body 1721 is drawn from the recess 1711 to the maximum extent so that the communication hole 1723 in the plunger body 1721 permits to communicate the first and second tubes 1712 and 1713 with each other. The sterilized water 15 can flow through the first tube 1712, communication hole 1723, and second tube 1713 between the reservoir 16 and the balloon 12.

Figure 4:
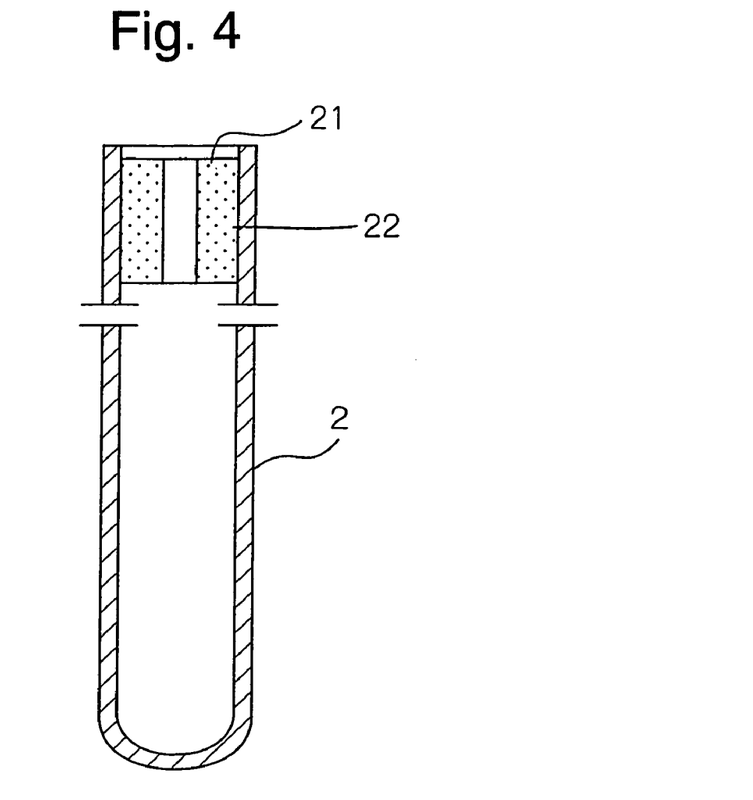
FIG. 4 is a longitudinal section view of another embodiment of a disinfectant casing that is one of constituents of the catheter set in accordance with the present invention.
Figure 5:
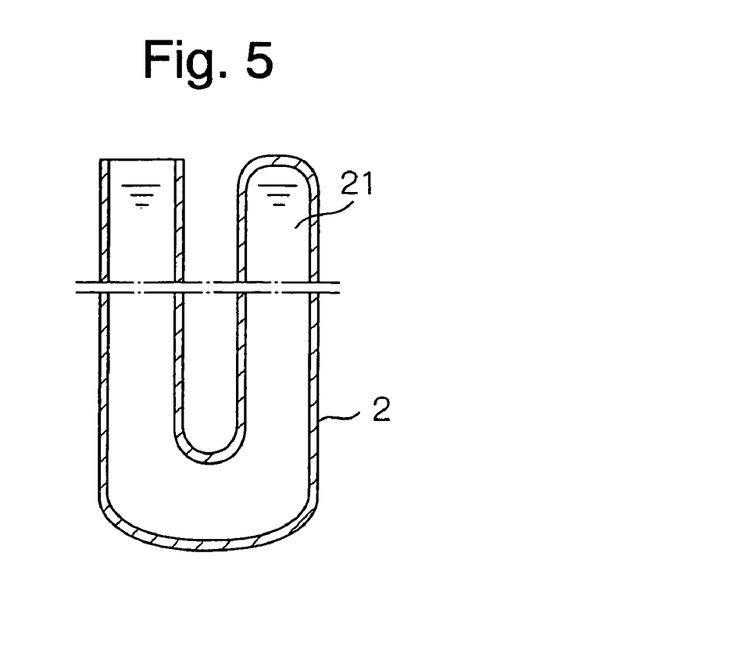
FIG. 5 is a longitudinal section view of still another embodiment of a disinfectant casing that is one of constituents of the catheter set in accordance with the present invention.

As shown in FIG. 4, an absorbing material 22, such as sponge or the like is mounted on an inner peripheral surface around an upper outlet of the disinfectant casing 2. The absorbing material 22 serves to absorb disinfectant liquid 21. When the catheter body 11 comes out from and enters the disinfectant casing 2, the catheter body 11 rubs the inner surface of the absorbing material 21 to be sterilized. Thus, it is unnecessary to fill the disinfectant liquid 21 in the disinfectant casing 2. Also, as shown in FIG. 5, the disinfectant casing 2 may be formed into a U-shaped configuration. This configuration will be convenient for accommodation and portage. The absorbing material 22 shown in FIG. 4 may be provided on an inner peripheral surface around an upper outlet of the U-shaped disinfectant casing 2 shown in FIG. 5.

Figure 6A:
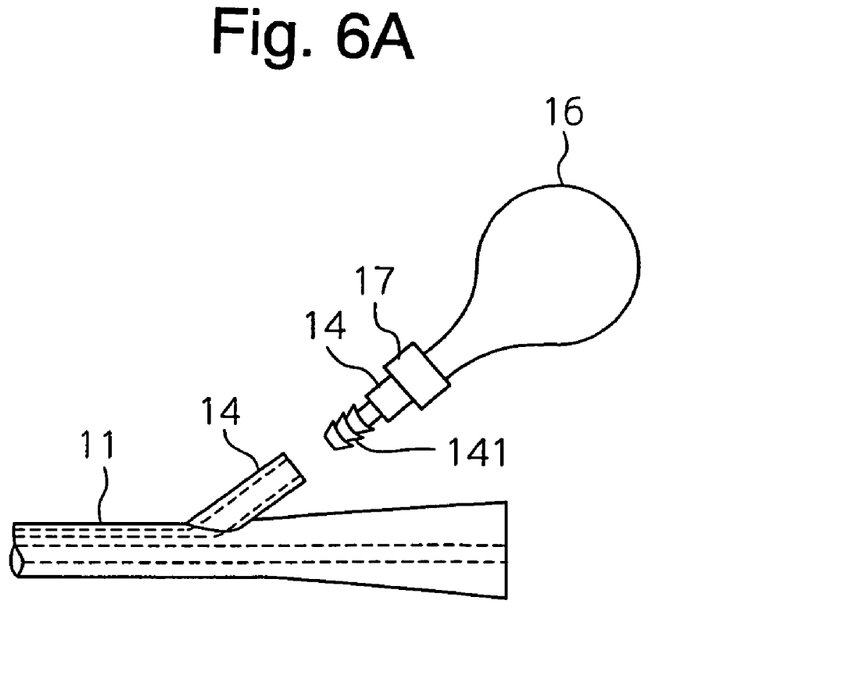
FIG. 6A is a side elevation view of another embodiment of a branched tube that is one of constituents of the catheter set in accordance with the present invention, illustrating the branched tube separated from a catheter body.
Figure 6B:
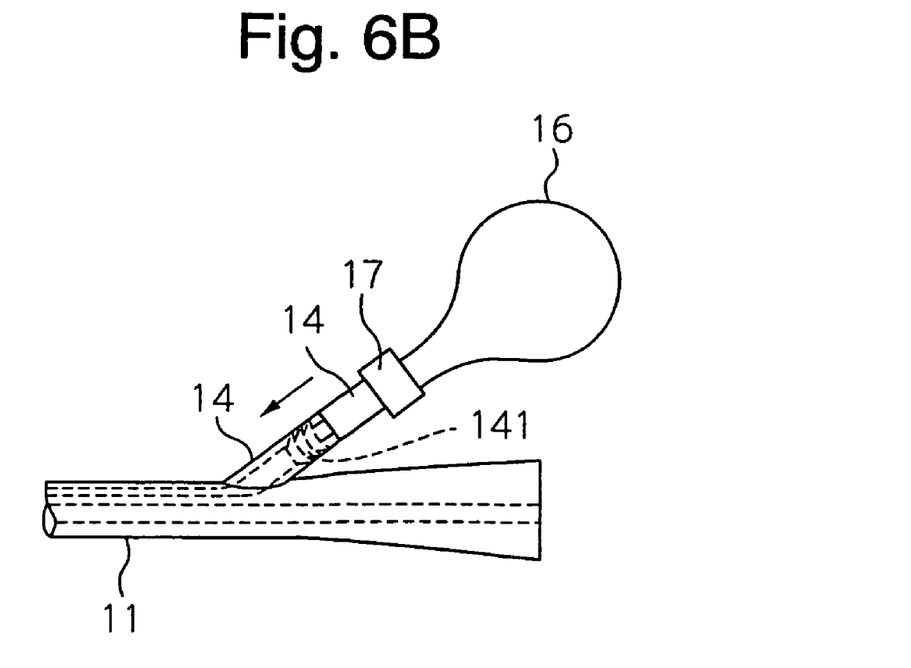
FIG. 6B is a view similar to FIG. 6A, illustrating the branched tube joined to the catheter body.

As shown in FIGS. 6A and 6B, the branched tube 14 may be detachably coupled to the catheter body 11 by a bamboo shoot type connector 141.

Figure 9:
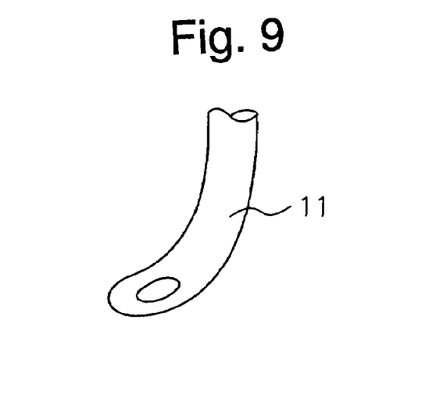
FIG. 9 is a plan view of a distal end of the catheter body that is one of constituents of the catheter set in accordance with the present invention.

As shown in FIG. 9, a distal end of the catheter body 11 may be formed into a curved configuration. This configuration will make it easy to insert the catheter body 11 into a urethra.

Figure 7A:
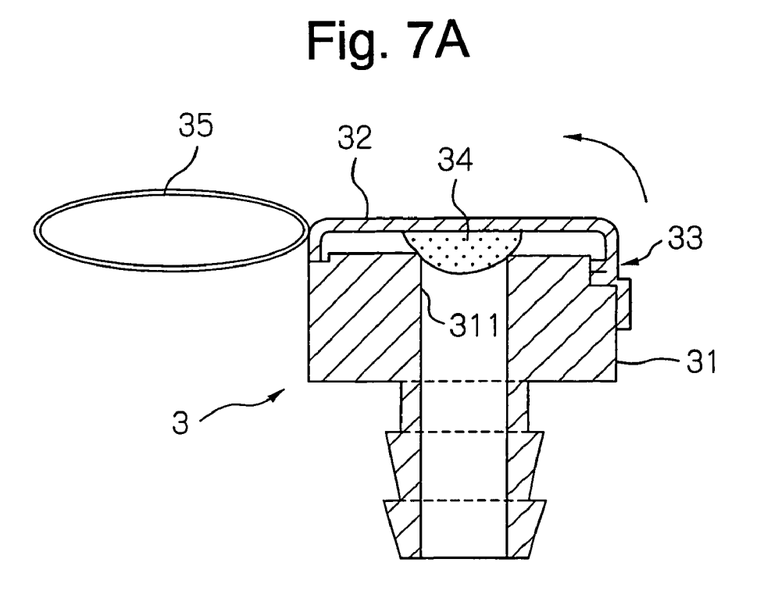
FIG. 7A a longitudinal section view of a cap that is one of constituents of the catheter set in accordance with the present invention, illustrating the cap in a closed position.
Figure 7B:
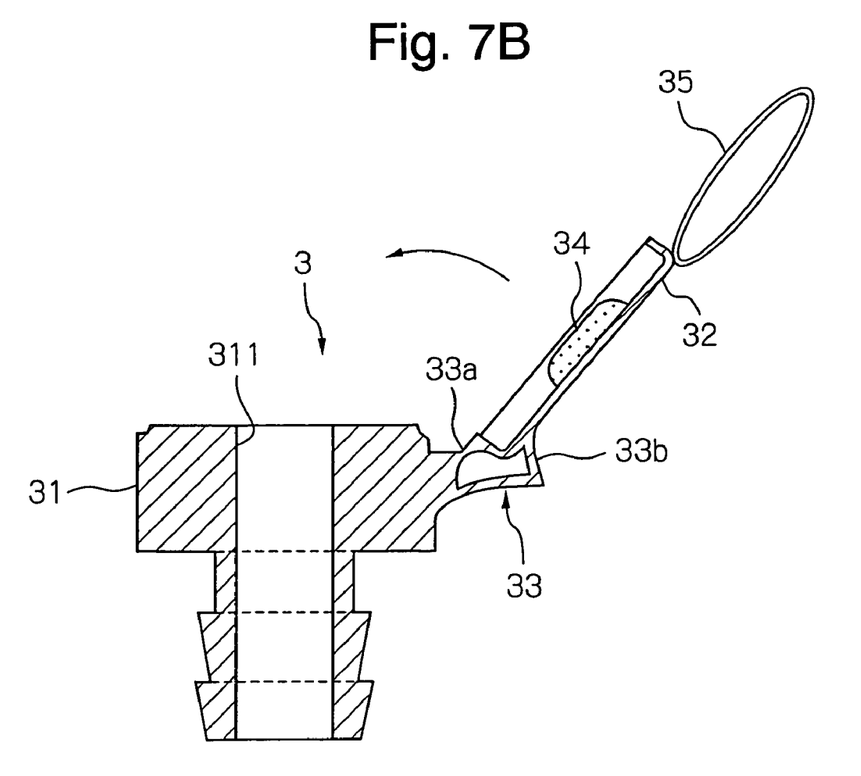
FIG. 7B is a view similar to FIG. 7A, illustrating the cap in an opened position.
Figure 8:
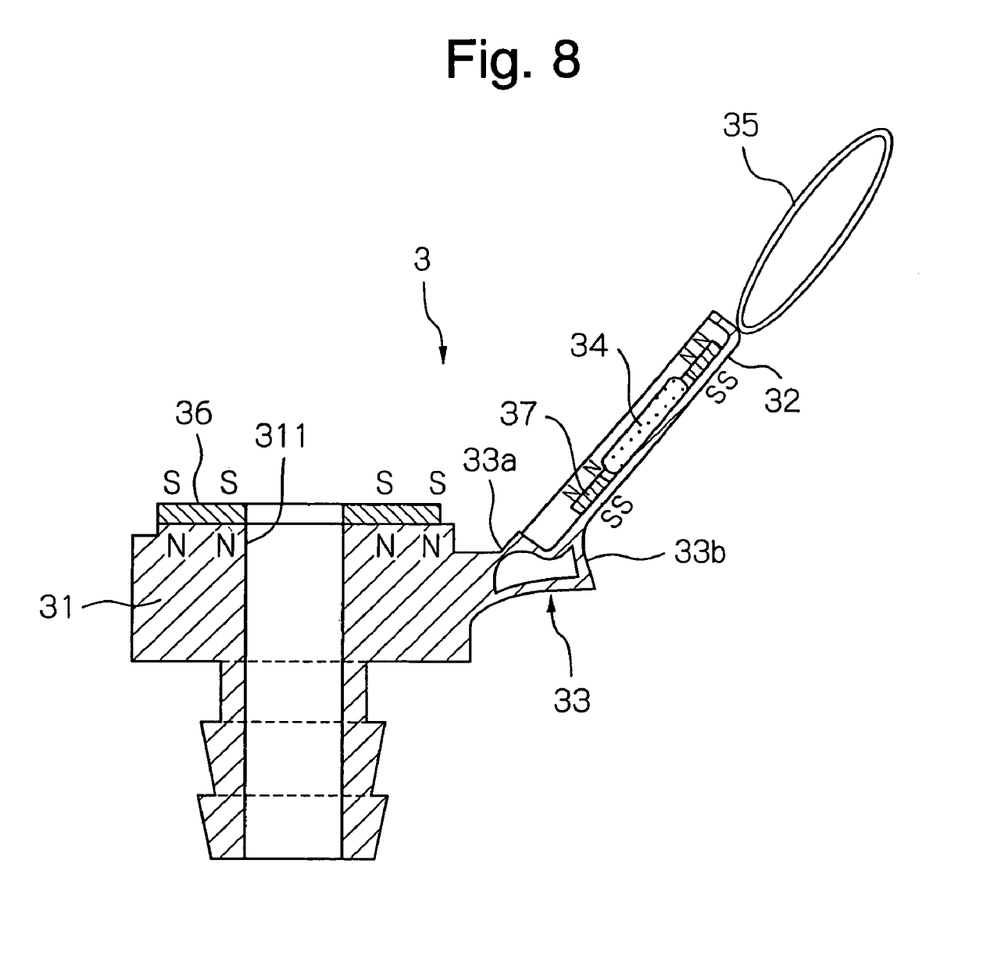
FIG. 8 a longitudinal section view of another embodiment of a cap that is one of constituents of the catheter set in accordance with the present invention, illustrating the cap in an opened position.

Referring now to FIGS. 7A, 7B, and 8, a detailed structure of the cap 3 will be explained below. FIGS. 7A and 7B show a first embodiment of a cap 3 of the present invention. The cap 3 includes a connection plug body 31, a lid body 32, and a hinge 33. The lid body 32 is coupled to the connection plug body 31 through the hinge 33. In the cap 3, the connection plug body 31, hinge 33, and lid body 32 are integrally formed of the same synthetic resin material. The lid body 32 is provided on a central area of an inner surface thereof with an engaging member 34 made of a resilient material (for example, silicone rubber, polyethylene, or the like). The lid body 32 is provided on an end thereof with a pull string 35.

The hinge 33, as shown in FIGS. 7A and 7B, includes a joint portion 33a which serves to join the lid body 32 to the connection plug body 31, and an elastically deformable portion 33b. The elastically deformable portion 33b actuates the lid body 32 to be closed by the elastic recovery force within a critical turning angle, but the portion 33b actuates the lid body 32 to be returned to the completely opened position by means of the buckling action of the portion 33b when the lid body 32 rotates over the critical turning angle (see FIG. 7B).

As shown in FIG. 7A, the engaging member 34 engages a peripheral edge of an outlet port 311 in the connection plug body 31 with the member 34 being resiliently deformed when the lid body 32 covers a top of the connection plug body 31, thereby maintaining the outlet port 311 in an airtight or liquid-tight condition.

Even if a person has limited use of hands or fingers, the lid body 32 can be easily opened and closed by hooking and pulling the pull string 35 by a person's palm or finger.

The cap 3 may be used, for example, as shown in FIGS. 1 and 2. FIG. 1 shows an example in which the cap 3 is attached to an external drain port of the catheter body 11 of the intermittent urethra self-retaining catheter set 10. Although the connection plug body 31 shown in FIGS. 1 and 2 is coupled to an inside of a port of a mating appliance, the connection plug body 31 may be coupled to the outside of the port.

FIG. 8 shows a second embodiment of the cap 3. In the second embodiment, an annular magnet 36 is secured to the upper surface of the connection plug body 31 and another annular magnet 37 is secured to the inner face of the lid body 32 around the engaging member 34. The magnets 36 and 37 are set to be 5 to 15 mm in diameter, 0.5 to 5.0 mm in thickness, and 100 to 2000 gauss in magnetic flux density. Magnetic poles on contact surfaces of the magnets 36 and 37 are directed in opposition to each other. In the illustrated embodiment, the upper and lower surfaces of the annular magnet 36 are set to be an S-pole and an N-pole while the upper and lower surfaces of the magnet 37 are set to be an N-pole and an S-pole. One of the annular magnets 36 and 37 may be replaced by an annular magnet made of a ferromagnetic material (for example, iron, samarium, nickel, cobalt, ferrite, or the like).

As shown in FIG. 8, when the cap 3 is in an opened position, the annular magnet 36 releases the outlet port 311 in the connection plug body 31 while the magnet 37 is spaced away from the plug body 31. When the cap 3 is in a closed position similar to FIG. 7A, both magnets 36 and 37 come into contact with each other and attract each other by their magnetic forces. Both magnets 36 and 37 are automatically aligned with the same central axis by their attraction forces immediately before the magnets 36 and 37 come into contact with each other. Even if the magnets 36 and 37 are a little shifted from each other, the engaging member 34 can automatically correct the misalignment by a manner described above.

When the cap 3 is in the closed position as shown in FIG. 1, the engaging member 34 closes the outlet port 311 in the connection plug body 31. When the magnets 36 and 37 are attached to each other, the engaging member 34 inside the annular magnet 37 comes into contact with the inner peripheral edge of the annular magnet 36 and the inner peripheral edge of the outlet port 311 in the connection plug body 31, thereby enhancing the air and liquid sealing in the cap 3. In addition, the engaging member 34 serves to guide the magnet 37 upon interconnection of the magnets 36 and 37.

Figure 10A:
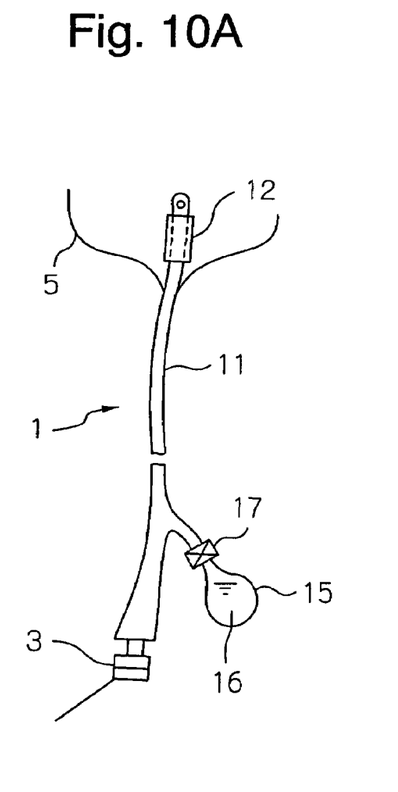
FIG. 10A is an explanatory view of an example of use of the catheter set in accordance with the present invention, illustrating a position where the catheter body has been just inserted into a bladder.
Figure 10B:
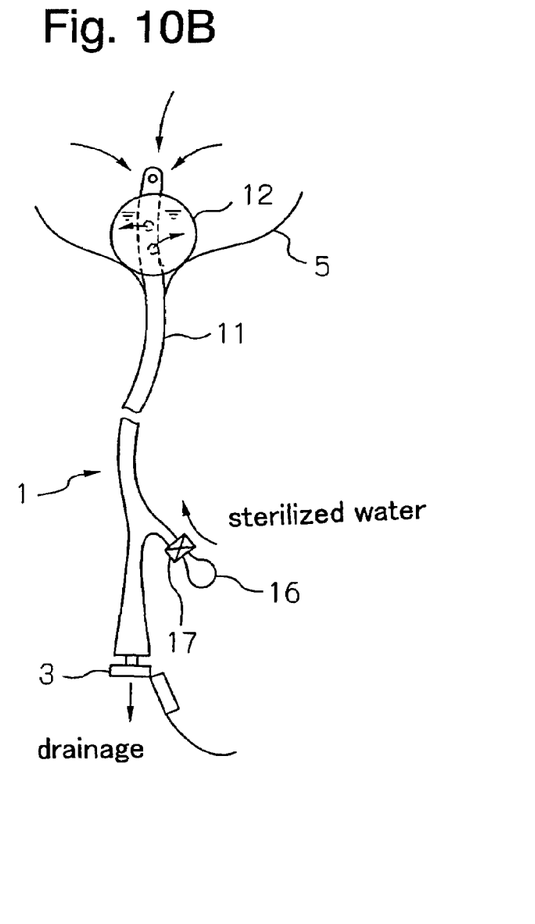
FIG. 10B is a view similar to FIG. 10A, illustrating a position where the catheter body is retained in the bladder.

By referring to FIGS. 10A and 10B, an example of use of the intermittent urethra self-retaining catheter set 10 in accordance with the present invention will be explained below. Firstly, the catheter unit 1 is removed from the disinfectant casing 2 and the catheter body 11 is inserted through a urethra into a bladder 5 (FIG. 10A). At this time, the balloon 12 is in a contracted position. Since the upper part of the catheter body 11 is reinforced by the reinforcement tube 18, a user can handle the catheter 11 readily without causing a proximate side of the catheter body 11 to be deformed irregularly.

Secondly, the user pulls the pull string 173 (FIG. 1) of the on-off valve 17 to bring the on-off valve 17 into an opened position (FIG. 3B). When the reservoir 16 is compressed manually, sterilized water 15 in the reservoir 16 flows into the balloon 12 to inflate the balloon 12 (FIG. 10B). Then, the user pushes the plunger 172 of the on-off valve 17 manually into the valve body 171 to bring the on-off valve 17 into a closed position (FIG. 3A). Consequently, the balloon 12 keeps its inflation.

The inflation of the balloon 12 retains the catheter unit 1 in the bladder 5. Next, the user pulls the pull string 35 of the cap 3 to open the outlet port 311 in the cap 3. Urine in the bladder 5 is drained through the urine-guiding passage 111 (FIG. 1) from the outlet port 311 to the outside.

When the retention is finished, the on-off valve 17 is opened to return the sterilized water 15 from the balloon 12 to the reservoir 16. Then, the balloon 12 returns to the original contracted position and the on-off valve 17 is closed again. After using the catheter unit 1, it is inserted into the disinfectant casing 2, the cap 3 closes the outlet port 311 of the cap 3. Under this condition, the catheter set 10 is stored at a suitable place.

In the cap 3, when a disabled patient hooks the pull string 35 to one's palm or finger toward the connection plug body 31, the lid body 32 covers a top of the connection plug body 31 by means of an elastic recovery force of the hinge 33, so that the engaging member 34 engages with a peripheral edge of an outlet port 311 in the connection plug body 31 in an airtight manner. At this time, even if the lid body 32 moves eccentrically, the engaging member 34 on the inner face of the lid body 32 is guided by the outlet port 311 in the connection plug body 31 to bring the lid body 32 into a regular position. Accordingly, the lid body 32 firmly engages the connection plug body 31 and leakage of urine can be prevented, since the engaging member seals the outlet port in an airtight or liquid-tight manner even if any clearance between the contact surfaces of the bodies 32 and 31 is caused.

In the case of opening the lid body 32, the lid body 32 will be opened by pulling the pull string strap 35 in the reverse direction against an elastic resistant force of the hinge 33. When the lid body 32 is turned over a critical angle, the lid body 32 is maintained in a completely open position by means of a buckling action of the hinge 33. Accordingly, it is not necessary for the user to intentionally keep the lid body 32 in the opened position.

According to the intermittent urethra self-retaining catheter set, the catheter unit can be retained in the bladder, for example, during half-day (daytime or nighttime), it is unnecessary to use a napkin, to require nursing, care or the like during the half-day. On the other hand, handling of the catheter set becomes more convenient, self-drainage can be done, and area of behavior for a user is not restrained. Since duration of time for retaining is relatively short, there is no possibility of urinary infectious disease.

POSSIBILITY OF UTILIZATION IN AN INDUSTRIAL FIELD

The intermittent urethra self-retaining set of the present invention is suitable for use by a patient suffered from a damaged spinal cord, a patient suffered from cerebrovascular disease, and a patient suffered from drainage disease due to congenital urethra deformity.

The invention claimed is:

1. An intermittent urethra self-retaining catheter set comprising a catheter unit, a disinfectant casing, and a cap;
    said catheter unit including: a catheter body having an urine-guiding passage and a water-guiding passage that extend along a longitudinal direction and are separated from each other, a balloon attached to a distal end of said catheter body in an inflatable manner and communicated to said water-guiding passage, an elastic plug attached to an intermediate portion of said catheter body, a branched tube bifurcated from said catheter body above said elastic plug and communicated to said water-guiding passage, a reservoir attached to a free end of said branched tube in a collapsible manner for storing a sterilized water, an on off valve attached to an intermediate portion of said branched tube, and a reinforcement tube inserted into an upper interior of said urine-guiding passage in said catheter body;
    said disinfectant casing being detachably fitted on said elastic plug in a sealing manner for containing a lower part of said catheter body below said elastic plug and for storing a disinfectant liquid;
    said cap being detachably fitted on a top portion of said catheter body for opening and closing an outlet port; and
    said on-off valve being adapted to open and close a passage in which said sterilized water flows between said reservoir and said balloon
    wherein said on off valve includes a valve body, a plunger, and a pull string, wherein said valve body includes a recess that supports said plunger to permit said plunger to reciprocate in said recess with a frictional resistance, a first tube communicated to said reservoir, and a second tube communicated to said branched tube, wherein said plunger includes a plunger body that can reciprocate in said recess with a frictional resistance, a flange, and a communication hole, and wherein said pull string is bound on said flange of said plunger to form a hoop.

2. A catheter set according to claim 1 wherein said branched tube is detachably connected to said catheter body.

3. A catheter set according to claim 1 wherein said cap includes a connection plug body, a hinge section, and a lid that are made of a synthetic resin material integrally together with one another, wherein an engaging member made of a flexible material is mounted on a central portion of an inner surface of said lid, and wherein a pull string is attached to an end of said lid.

4. A catheter set according to claim 3 wherein a first annular magnet is secured to a top surface of said connection plug body and a second annular magnet is secured to an inner surface of said lid to surround said engaging member.

5. A catheter set according to claim 1 wherein an absorbing material is mounted on an inner peripheral surface around an upper outlet of said disinfectant casing.

6. A catheter set according to claim 1 wherein a distal end of said catheter body is formed into a curved configuration.

7. A catheter set according to claim 1 wherein the catheter body is a unitary structure.

* * * * *